United States Patent [19]

van den Berg et al.

[11] Patent Number: 4,691,572

[45] Date of Patent: Sep. 8, 1987

[54] TRANSDUCING DEVICE FOR CONTACTLESS ULTRASONIC INSPECTION OF PIPELINES OR TUBINGS

[75] Inventors: Wilhemus H. van den Berg; Marinus H. Homs, both of Amsterdam, Netherlands; Bob P. J. van Oorschot, Aberdeen, United Kingdom

[73] Assignee: Shell Oil Company, Houston, Tex.

[21] Appl. No.: 763,845

[22] Filed: Aug. 8, 1985

[30] Foreign Application Priority Data

Aug. 9, 1984 [GB] United Kingdom ............... 8420244

[51] Int. Cl.$^4$ ........................................... G01N 29/04
[52] U.S. Cl. ....................................... 73/643; 73/622; 73/638
[58] Field of Search ................. 73/643, 622, 638, 623, 73/635, 639, 637

[56] References Cited

U.S. PATENT DOCUMENTS

| | | | |
|---|---|---|---|
| 3,850,028 | 11/1974 | Thompson et al. | 73/643 |
| 4,092,868 | 6/1978 | Thompson et al. | 73/643 |
| 4,307,615 | 12/1981 | Robinson | 73/643 |
| 4,314,479 | 2/1982 | Spijkerman | 73/643 |

OTHER PUBLICATIONS

Krautcramer and Krautcramer, Ultrasonic Testing of Materials, second edition, 1977, pp. 8–11.

Maxfield, Kuramoto and Hulbert, "Using EMATS for High Temperature Ultrasonics," *Through the Eyes of an Eagle,* 11th World Conference on Nondestructive Testing (Conference of Nov. 3–8, 1985), vol. 2, pp. 917–924.

*Primary Examiner*—Anthony V. Ciarlante

[57] ABSTRACT

A transducing device for contactless ultrasonic inspection of pipelines or tubings is provided. The device has a means for electromagnetically generating elastic waves within the wall of the pipeline or tubing to be inspected and means for mounting and moving said device along a pipeline or tubing. The generating means may be a magnet and at least one transmitting coil, with the transmitting coil arranged on one of the poles of the magnet. The poles of the magnet are directed towards the wall of the pipeline or tubing under inspection.

17 Claims, 3 Drawing Figures

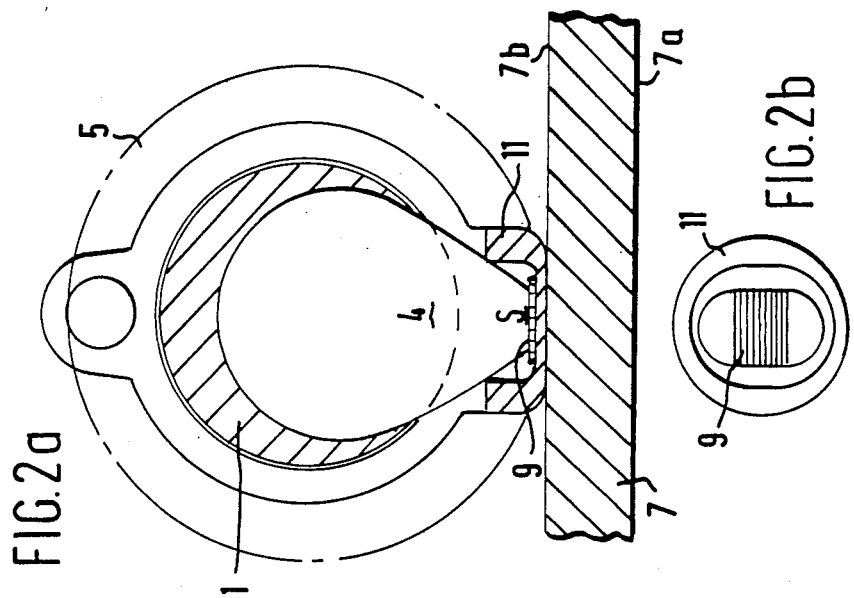
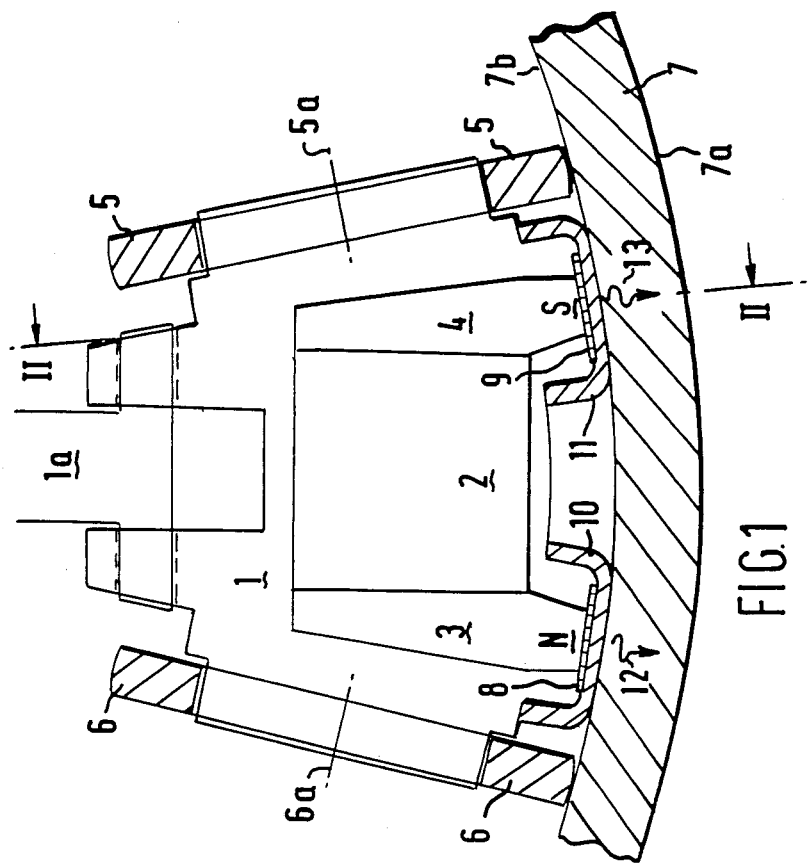

TRANSDUCING DEVICE FOR CONTACTLESS ULTRASONIC INSPECTION OF PIPELINES OR TUBINGS

BACKGROUND OF THE INVENTION

The invention relates to a transducing device for contactless ultrasonic inspection of pipelines or tubings.

Ultrasonic inspection of pipelines, risers and the like is usually carried out by pigs which move through the pipeline to be inspected. These pigs are usually provided with means for transmitting ultrasonic pulses into the pipeline wall and means for receiving reflected pulses. The reflected pulses are processed in a suitable way in order to obtain information about the condition of the pipeline wall. Such ultrasonic measurements based upon the reflection principle are known to those skilled in the art and will not be described in detail.

Conventional ultrasonic transducers need an acoustic coupling medium between the transducer and the wall under inspection in order to adapt their respective acoustic impedances. A liquid is normally used as such a coupling medium. However, in many situations it is very difficult or even impossible to use such a liquid acoustic couplant e.g. in a gas environment or on hot surfaces.

However, U.S. Pat. No. 4,092,868 discloses a device for contactless internal ultrasonic inspection of pipelines; the disclosed device is provided with a means for inducing ultrasonic energy (so-called "Lamb" waves) electromagnetically in a metal object to be inspected. The "Lamb" waves fill the entire cross section of the object under inspection and are not just a narrow beam of ultrasonic energy. The device as disclosed in U.S. Pat. No. 4,092,868 is not suitable for focusing ultrasonic energy in the object under inspection.

These and other limitations and disadvantages of the prior art are overcome by the present invention and improved apparatus are provided for inspecting tubing and the like employing ultrasonic energy employing no coupling medium.

SUMMARY OF THE INVENTION

It is an object of the invention to provide an ultrasonic electromagnetic transducer, for inspection of pipelines, which requires no acoustic couplant between transducer and tube wall, said device being able to produce and to direct an ultrasonic beam in an accurate manner.

It is another object of the present invention to provide a self-centering ultrasonic electromagnetic transducer for internal inspection of pipelines, capable of passing local obstacles within the said pipeline.

It is another object of the invention to provide an ultrasonic electromagnetic transducer for inspection of pipelines or tubings which is not restricted to the use of "Lamb" waves, but generates elastic shear waves in the object under inspection.

In a preferred embodiment of the present invention a transducing device for contactless ultrasonic inspection of pipelines or tubings is provided. This device contains means for electromagnetically generating elastic waves within the wall of the pipeline or tubing to be inspected, means for mounting and moving said device along a pipeline or tubing. The means for generating elastic waves is preferably a magnet and at least one transmitting coil. The transmitting coil is preferably arranged on one of the poles of the magnet. The poles of the magnet are directed towards the wall of the pipeline or tubing under inspection, during use.

These and other objects and features of the present invention will become apparent from the following detailed description wherein reference is made to the Figures in the accompanying drawings.

BRIEF DESCRIPTION OF THE DRAWINGS

FIG. 1 represents an axial view of one embodiment of the ultrasonic transducing device of the present invention.

FIG. 2a represents a cross section of the device of FIG. 1 along the lines II—II.

FIG. 2b represents a detail of FIG. 2a.

DESCRIPTION OF PREFERRED EMBODIMENTS

Referring now to FIG. 1, a device having a housing 1 and a magnetic means 2 has been depicted. In a preferred embodiment the magnetic means is a permanent magnet 2 provided with focusing discs 3 and 4. These discs 3, 4 are mounted in such a way that a U-shaped magnetic yoke is provided with conical poleshoes N and S. The said magnetic means 2 is connected mechanically to the housing 1 by any suitable means (which are not shown for reasons of clarity).

The housing 1 is provided with support wheels 5 and 6 which support the housing and the magnet against the pipeline wall 7 (wheels 5 and 6 are shown in cross section). The wheels 5 and 6 rotate about the axes 5a and 6a respectively (schematically shown). The housing 1 is further connected mechanically in any suitable way to a pigbody for moving the ultrasonic device through the pipeline or tubing under inspection. This mechanical connection may be by way of example, a hinge 1a. For reasons of clarity the pigbody and mechanical connections have not been shown, and only part of the pipeline wall 7 has been represented. Other mechanical connections may be employed for exterior inspections, as are known in the art. Transmitting coils 8 and 9 are arranged on the said conical poleshoes N and S, respectively.

The transmitting coils 8 and 9 are arranged in any suitable way on the said poleshoes, which, in use, are directed towards the pipeline wall 7b. In advantageous embodiments of the invention the thickness of these coils is 0.1 to 0.5 millimeters and a suitable excitation frequency range of the coils is 2 to 4 megahertz.

The device of the invention may also have protection cups 10, 11 for protection of transmitter coils 8, 9. Further, receiving coils may also be arranged on the conical poleshoes N and S for receiving the ultrasonic reflected pulses. (These receiving coils have not been represented for reasons of clarity).

The operation of the device of the invention is as follows: The transmitter coils 8 and 9 which are arranged on the said poleshoes N and S of the magnet respectively are excited with a suitable rf pulse, for example 2 megahertz, and induce rf eddy currents in the surface of the electrically conductive pipeline wall 7 under inspection. As a continuous magnetic induction is present, Lorentz forces will act on the material under inspection and due to the high excitation frequency of the transmitting coils ultrasonic elastic waves 12 and 13 will be generated in the wall 7.

The ultrasonic waves are reflected against the rear surface 7a of the wall 7 and return to the front surface 7b of the wall 7.

The reverse process then applies for detection, i.e. a voltage is induced in the receiving coil or coils by means of electromagnetic induction and the received signal is processed further in order to derive information on the condition of the pipeline wall. As already indicated earlier, the principle underlying these measurements is known as such to those skilled in the art and will not be discussed further.

FIG. 2a represents a cross section of the embodiment of FIG. 1 along the focusing disc 4 (lines II—II). The same reference numerals as in FIG. 1 have been used.

FIG. 2b represents the side of the device of FIG. 2a which, in use, is directed towards the pipeline wall 7b. A linear coil 9 arranged on the pole S of the focusing disc 4 and surrounded by a protection cup 11 have been shown.

It will be appreciated that any shape and dimensions of the megnetic means, transmitting coils and receiving coils may be used, provided that the transmitting coils are arranged on at least one of the poles of the magnetic means, which are directed towards the pipeline wall.

In preferred embodiments of the invention a so-called pancake (or spirally wound) coil can be used.

It will be appreciated that the transmitter and receiver coils may be combined on one pole of the magnet. Further, the permanent magnet and the focusing discs may be embedded in a suitable material, for example epoxy resin.

In another preferred embodiment one of the poles of the magnetic means contains the transmitter coil while the other pole contains the receiving coil. A suitable material for the magnet is low reluctance steel. The portions of the conical poleshoes, which are directed towards the pipeline wall, may be made of material for preventing the excitation of eddy currents in the discs. Although described herein by way of a permanent magnet for magnet means 2, the invention is clearly not restricted to only the use of a permanent magnet. For some alternate embodiments of the invention an electromagnet may be used.

Various modifications of the present invention will become apparent to those skilled in the art from the foregoing description and accompanying drawings. Such modifications are intended to fall within the scope of the appended claims.

What is claimed is:

1. A transducing device for contactless ultrasonic inspection of a conductive plate material, comprising:
   means for electromagnetically generating focused transverse elastic waves within said plate material to be inspected effective to drive said elastic waves through the plate material causing reflections of the elastic waves from the rear side of the plate material; and
   means for mounting and moving said means for generating along said material.

2. A transducing device for contactless ultrasonic inspection of a conductive plate material, comprising:
   magnet means having two poles and at least one transmitting coil disposed on one of the poles of said magnet means for electromagnetically generating elastic shear waves within said plate material;
   means for focusing said elastic shear waves through the plate material causing reflections of the elastic shear waves from the other side of the plate material, said means for focusing comprising a focusing disc of the magnet means attached to a conically tapered poleshoe at each of the poles; and
   means for mounting said magnet means to dispose said poleshoes of said magnet means towards said material and for moving said magnet means along said material.

3. The device as claimed in claim 2 wherein the thickness of said coils is 0.1 to 0.5 millimeters.

4. The device as claimed in claim 2 wherein the exciting frequency range of the transmitting coil is 2 to 4 megahertz.

5. A transducing device for internal contactless ultrasonic inspection of a pipeline or the like, comprising:
   magnet means having two poles and at least one transmitting coil disposed on one of the poles of said magnet means for electromagnetically generating transverse elastic waves within a wall of said pipeline;
   means for focusing said transverse elastic waves through the wall of the pipeline effective to cause reflections of the transverse elastic waves from the rear of the wall, said means for focusing comprising a focusing disc of the magnet means attached to a conically tapered poleshoe at each of the poles; and
   means for mounting said magnet means to dispose said poleshoes of said magnet means towards said pipeline wall and for moving said magnet means through said pipeline.

6. The device as claimed in claim 5 wherein the said magnet means is a permanent magnet.

7. The device as claimed in claim 6 wherein said magnet is composed of low reluctance steel and wherein said poles are provided with material for preventing the excitation of eddy currents in said poles.

8. The device as claimed in claim 7 wherein said permanent magnet and focusing discs are embedded in epoxy resin.

9. The device as claimed in claim 5 wherein the said magnet means is an electromagnet.

10. The device as claimed in claim 5, further comprising a protection cup on the poleshoes of said magnet means.

11. The device as claimed in claim 5 wherein said transmitting coil is a spiral coil.

12. The device as claimed in claim 5 wherein said transmitting coil is a linear coil.

13. The device as claimed in claim 5 further comprising at least one receiving coil disposed on one of the poles of the said magnet means.

14. The device as claimed in claim 5 wherein said magnet means is provided with support wheels.

15. The device as claimed in claim 5 wherein the thickness of said coils is 0.1 to 0.5 millimeters.

16. The device as claimed in claim 5 wherein the exciting frequency range of the transmitting coil is 2 to 4 megahertz.

17. A device for contactless inspection of a pipeline wall, comprising:
   a transducer for generating focused transverse elastic waves having an exciting frequency in the 2 to 4 megahertz range, said transducing device comprising:
   a permanent magnet formed of low reluctance steel and having two poles;
   a focusing disc at each of the poles of the permanent magnet;

a conically tapered pole shoe connected to each focusing disc; and at least one transmitting coil having a thickness of 0.1 to 0.5 millimeters disposed on one of the poles of said permanent magnet between the poleshoe and the pipeline wall for electromagnetically generating focused transverse elastic waves within the wall of the pipeline directed to reflect from the rear of the wall;

an epoxy resin surrounding and embedding the permanent magnet and the focusing discs;

means for moving the transducer through said pipeline;

self-centering means for mounting the transducer to the means for moving the transducer in order to dispose the poleshoes towards the pipeline wall; and at least one receiving coil disposed on one of the poles of the permanent magnet for receiving the transverse elastic waves reflected from the rear of the pipeline wall.

* * * * *